US00PP35299P2

(12) United States Plant Patent
Camus

(10) Patent No.: US PP35,299 P2
(45) Date of Patent: Aug. 8, 2023

(54) ***HYDRANGEA* PLANT NAMED 'CAMFRE29'**

(50) Latin Name: ***Hydrangea* x *macrophylla***
Varietal Denomination: CAMFRE29

(71) Applicant: Sicamus, Angers (FR)

(72) Inventor: Christophe Camus, Angers (FR)

(73) Assignee: SICAMUS

( * ) Notice: Subject to any disclaimer, the term of this patent is extended or adjusted under 35 U.S.C. 154(b) by 0 days.

(21) Appl. No.: 17/958,049

(22) Filed: Sep. 30, 2022

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

*Primary Examiner* — Karen M Redden
(74) *Attorney, Agent, or Firm* — Cassandra Bright

(57) ABSTRACT

A new and distinct cultivar of *Hydrangea* plant named 'CAMFRE29' is disclosed, characterized by lace-cap inflorescences, and violet-blue sepals with deeper purple picotee along a serrated margin. Plants have compact habits, and green foliage with a slight purple tine along the margin. The new variety is a *Hydrangea*, typically produced as an outdoor ornamental plant.

2 Drawing Sheets

Figure 1:
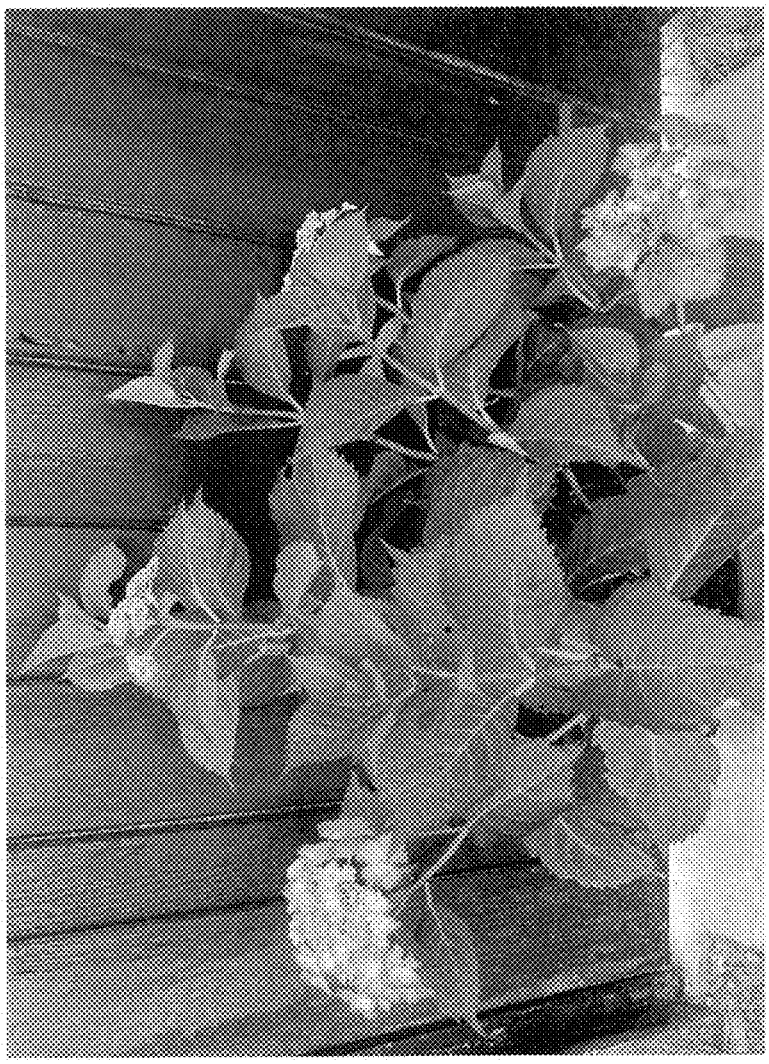

Latin name of the genus and species: *Hydrangea* x *macrophylla.*

Variety denomination: 'CAMFRE29'.

BACKGROUND OF THE INVENTION

The new cultivar is a product of a planned breeding program conducted by the inventor, at a commercial nursery in Angers, France. The crossing resulting in the new variety was made during 2008.

The seed parent is an unpatented proprietary variety of *Hydrangea macrophylla*. The pollen parent is a different unpatented proprietary variety of *Hydrangea macrophylla.*

The new variety was found and selected by the inventor in 2009 at the same nursery in Angers, France.

Asexual reproduction of the new cultivar 'CAMFRE29' was first performed during July of 2010 in Angers, France, by vegetative cuttings. Through subsequent propagation, multiple additional generations have been reproduced, having shown that the unique features of this cultivar are stable and reproduced true to type

SUMMARY OF THE INVENTION

The cultivar 'CAMFRE29' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAMFRE29'. These characteristics in combination distinguish 'CAMFRE29' as a new and distinct *Hydrangea* cultivar:

1. Deeply serrated and picoteed margins on all sepals.
2. Sepals are slightly yellow at the early flowering stage.

3. Very floriferous.
4. Foliage has slight purple edge.

PARENT COMPARISON

Plants of 'CAMFRE29' are similar to plants of the seed parent in most horticultural characteristics, however, plants of 'CAMFRE29' differ in the following:

1. Sepals of the new variety have deeper margins than sepals of the seed parent.
2. Sepals of the new variety are slightly yellow at the early flowering stage, while sepals of the seed parent are not.
3. Foliage of the new variety has a slight purple edge, while foliage of the seed parent does not.
4. The new variety is more compact than the seed parent.

Plants of 'CAMFRE29' are similar to plants of the pollen parent in most horticultural characteristics, however, plants of 'CAMFRE29' differ in the following:

1. Sepals of the new variety have deeper margins than sepals of the pollen parent.
2. Sepals of the new variety are slightly yellow at the early flowering stage, while sepals of the pollen parent are not.
3. The new variety has more flowers and better repeat blooming than the pollen parent.
4. The new variety is a more compact plant than the pollen parent.

COMMERCIAL COMPARISON

Plants of the new cultivar *Hydrangea* 'CAMFRE29' can be compared to the commercial variety *Hydrangea macrophylla* 'SMHMEPSILON', U.S. Plant Pat. No. 28,974. Plants of 'CAMFRE29' are similar to plants of 'SMHMEPSILON' in most horticultural characteristics, however, plants of 'CAMFRE29' differ in the following:

1. Sepals of the new variety have deeply serrate margins not found on the sepals of 'HMUPSI'.
2. Sepals of the new variety have distinctively picotee margins not found on the sepals of 'HMUPSI'.

Plants of the new cultivar *Hydrangea* 'CAMFRE29' can be compared to the commercial variety *Hydrangea macrophylla* 'HORTFIRE', U.S. Plant Pat. No. 29,058. Plants of 'CAMFRE29' are similar to plants of 'HORTFIRE' in most horticultural characteristics, however, plants of 'CAMFRE29' differ in the following:

1. Both varieties have bicolor sepals with picotee, however, the new variety has purple tones; this comparator has pink tones.
2. New variety is a lace-cap; this comparator is a mophead.
3. Sepals of the new variety have deep wavy margins, while sepals of 'HORTFIRE' do not.

BRIEF DESCRIPTION OF THE PHOTOGRAPHS

The accompanying photograph in FIG. 1 illustrates in full color a typical plant of 'CAMFRE29' grown outdoors Camarillo, Calif. This plant is approximately 2-3 years old, grown in a 5-gallon container.

Figure 2:
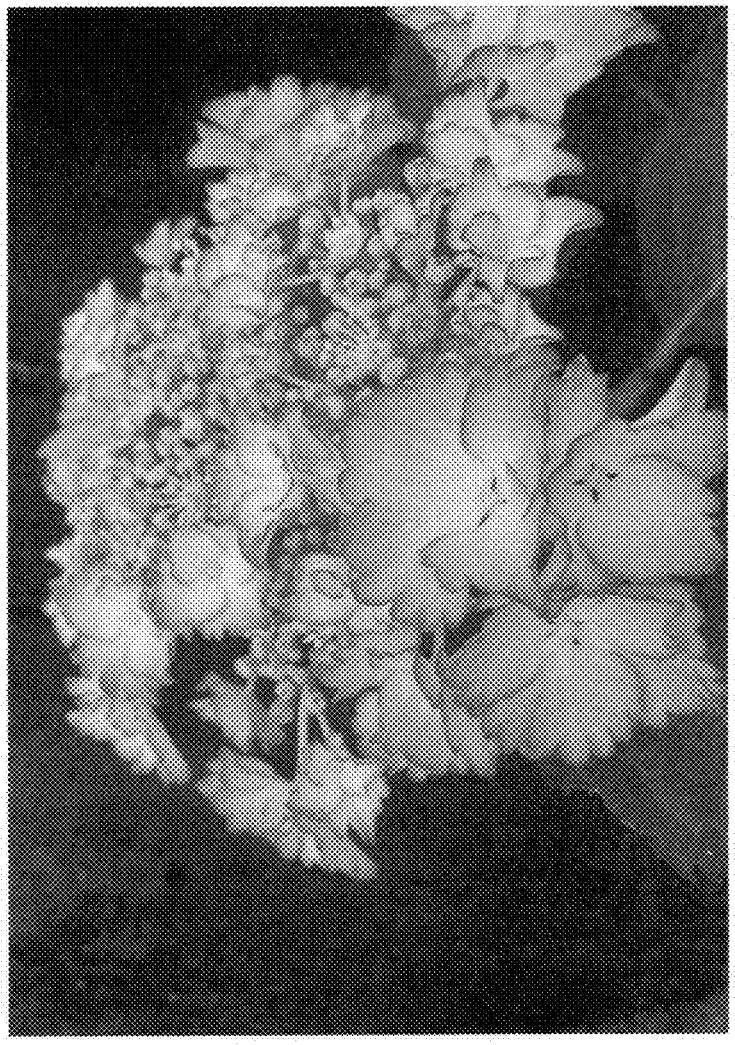

FIG. 2 illustrates in full color a close up of an inflorescence of 'CAMFRE29'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'CAMFRE29' plants grown outdoors in Camarillo, Calif. The plants were about 2 years old. Temperatures ranged from 12° C. to 15° C. at night to 18° C. to 27° C. during the day. No artificial light, photoperiodic treatments were given to the plants. Measurements and numerical values represent averages of typical plant types.

Botanical classification: *Hydrangea macrophylla* 'CAMFRE29'.

PROPAGATION

Typical method: Softwood cuttings.
Root initiation: Approximately 20 days.
Time to produce rooted cutting: 60 days during summer.
Roots: Thick to thin, freely branching, fibrous, dense. White to brown in color, not accurately measured with R.H.S. chart.

PLANT

Plant shape: Slightly flattened orbicular.
Growth habit: Outward and upward.
Height: 51 cm.
Plant spread: 63.5 cm.
Pot size of plant described: 3-gallon container.
Age of plant described: Approximately 2 years.
Growth rate: Moderate.
Plant vigor: Good.
Stems/branches:
- *Branching*.—Basal.
- *Number of main stems/branches*.—9 to 12.
- *Shape*.—Rounded.
- *Color*.—Immature: RHS Yellow-Green 144C. Mature: RHS Yellow-Green 144A Old growth: RHS Greyed-Brown N199B.
- *Length*.—35 to 39 cm.
- *Width*.—9 to 11 mm.
- *Aspect*.—15° to 65°.
- *Strength*.—Moderately strong.
- *Pubescence*.—None.
- *Internode length*.—6 to 9 cm.
- *Lenticels*.—Mature branches densely covered in lenticels. Colored near Greyed-Purple 187A. Irregularly shaped, wither round or elliptic. Size of round lenticels about 1.5 mm in diameter. Elliptic shaped lenticels approximately 2 mm wide and 3 mm to 5 mm long.

FOLIAGE

Leaf:
- *Arrangement*.—Opposite.
- *Shape*.—Ovate.
- *Length*.—11 to 14 cm.
- *Width*.—7 to 9 cm.
- *Apex*.—Acuminate.
- *Base*.—Obtuse to broad tapered.
- *Margin*.—Dentate.
- *Texture of top surface*.—Glabrous, turning very slightly pubescent with age.
- *Texture of bottom surface*.—Glabrous.
- *Color*.—Young foliage upper side: Near RHS Green 137A. Young foliage under side: Near RHS Green 138A. Mature foliage upper side: Near RHS Green 139A margin lightly tinged greyed-purple 187A. Mature foliage, under side: Near RHS Green N138B.

Venation:
- *Type*.—Pinnate.
- *Color*.—Upper side: Near RHS Yellow-Green 144B. Under side: Near RHS Yellow-Green 145B.

Petiole:
- *Length*.—2 cm.
- *Width*.—4 mm.
- *Color*.—Upper side: RHS Yellow-Green N144D. Under side: RHS Yellow-Green 145A. Upper side: Very slight pubescence. Under side: Very slight pubescence. Anthocyanin at nodes: Slight flush near Greyed-Purple 187A.

INFLORESCENCE

Natural flowering season: Summer.
Inflorescence type: Lace-cap.
Corymb:
- *Shape*.—Flat, disc shaped.
- *Height*.—6 to 8 cm.
- *Diameter*.—Average 17 cm.

Fragrance: Faint, fresh scent.
Sterile flowers:
- *Flowers per inflorescence*.—30 to 50.
- *Aspect*.—Upright and/or outwardly facing.
- *Shape*.—Round.
- *Arrangement*.—Overlapping whorl.
- *Diameter*.—4.5 cm.
- *Depth*.—1.0 cm (excluding pedicel).
- *Persistent or self-cleaning*.—Persistent.

Bud:
*Bud length.*—6 mm.
*Bud diameter.*—4 mm.
*Bud shape.*—Obovate.
*Bud color.*—RHS Green-White 157A.
Sepals:
*Number per flower.*—5.
*Arrangement.*—Strongly overlapping whorl.
*Shape.*—Broad deltate.
*Tip.*—Acute.
*Base.*—Truncate.
*Margin.*—Crenate. Frilly during opening stages.
*Length.*—2.0 to 2.5 cm.
*Width.*—2.0 to 3.0 cm.
*Texture.*—Upper side: Smooth, soft. Under side: Smooth, soft.
*Color.*—When Opening, Upper side: RHS Yellow-White 158D. Marginal picotee near Purple 77A. Flush extending from margin near Purple 77B. When Opening, Under side: RHS Yellow-White 158D. Marginal picotee near Purple 77A. Flush extending from margin near Purple 77B. Fully Opened, Upper side: RHS Violet-Blue 91D with overall flush near 91B and 91C. Marginal picotee near Violet N88A. Fully Opened, Under side: RHS Violet-Blue 91D with overall flush near 91C. Marginal picotee near Violet N88A.
Pedicel:
*Length.*—3 cm.
*Diameter.*—2 mm.
*Angle.*—About 45° to 135° from center.
*Strength.*—Good, flexible.
*Texture.*—Lightly pubescent.
*Color.*—RHS Yellow-White 155D flushed near base Purple-Violet N81C. Blotch near base near Purple N79B.
Fertile flowers:
*Flowers per inflorescence.*—150 to 250.
*Aspect.*—Upright.
*Shape.*—Stellate.
*Diameter.*—5 to 7 mm.
*Depth.*—3 mm. Stamens protruding to 6 mm.
*Persistent or self-cleaning.*—Self-cleaning.
Bud:
*Bud length.*—3 mm.
*Bud diameter.*—3 mm.
*Bud shape.*—Orbicular.
*Bud color.*—RHS Green-White 157A flushed Purple-Violet N82C.
Sepals:
*Number per flower.*—5.
*Arrangement.*—Stellate.
*Shape.*—Elliptic.
*Tip.*—Acute.
*Base.*—Flat.
*Margin.*—Entire.
*Length.*—3 mm.
*Width.*—2 mm.
*Texture.*—Upper side: Smooth, soft. Under side: Smooth, soft.
*Color.*—When Opening, Upper side: RHS Green-White 157C. When Opening, Under side: RHS Green-White 157C. Fully Opened, Upper side: RHS Violet-Blue 97B flushed 97A. Fully Opened, Under side: RHS Violet-Blue 97B flushed 94C.
Pedicel:
*Length.*—5 mm.
*Diameter.*—2 mm.
*Angle.*—15° to 135°.
*Strength.*—Good.
*Texture.*—Smooth.
*Color.*—RHS Yellow-Green 145B.

REPRODUCTIVE ORGANS

Sterile flower: Central, globular structure with no definable parts.
Fertile flower:
Stamen:
*Number.*—10 to 12.
*Filament length.*—3 to 6 mm.
*Filament color.*—RHS White 155B.
Anther:
*Shape.*—Rounded, basifixed.
*Length.*—About 1 mm.
*Color.*—RHS Yellow-White 158A.
*Pollen amount.*—Scant to none.
*Pollen color.*—RHS Yellow-White 158C.
Pistil:
*Number.*—1.
*Length.*—3 mm.
Stigma:
*Shape.*—3-parted.
*Color.*—RHS Green-White 157D.
*Style length.*—2 mm.
*Style color.*—RHS Green-White 157D.
*Ovary color.*—RHS Green-White 157D.

OTHER CHARACTERISTICS

Disease resistance: Neither resistance nor susceptibility to the normal diseases and pests of *Hydrangea* has been observed.
Drought tolerance: None.
Temperature tolerance: USDA Zones 6 to 9 reliably, Zone 5 with protection from the cold.
Fruit/seed production: Not observed to date.

What is claimed is:

1. A new and distinct cultivar of *Hydrangea* plant named 'CAMFRE29' as herein illustrated and described.

* * * * *